(12) United States Patent
Pawluczyk

(10) Patent No.: US 6,975,891 B2
(45) Date of Patent: Dec. 13, 2005

(54) RAMAN SPECTROSCOPIC SYSTEM WITH INTEGRATING CAVITY

(75) Inventor: Romuald Pawluczyk, Ontario (CA)

(73) Assignee: NIR Diagnostics Inc., Ontario (CA)

( * ) Notice: Subject to any disclaimer, the term of this patent is extended or adjusted under 35 U.S.C. 154(b) by 332 days.

(21) Appl. No.: 10/032,145

(22) Filed: Dec. 21, 2001

(65) Prior Publication Data

US 2003/0120137 A1 Jun. 26, 2003

(51) Int. Cl.$^7$ ............................. A61B 5/00; G01J 3/44; G01N 21/65
(52) U.S. Cl. ...................... 600/310; 600/316; 356/301; 250/339.12; 250/340
(58) Field of Search .................................. 600/310, 317, 600/316, 476; 356/301, 215, 236; 250/339.07, 339.12, 340

(56) References Cited

U.S. PATENT DOCUMENTS

| | | | |
|---|---|---|---|
| 4,127,329 A | 11/1978 | Chang et al. | |
| 4,310,246 A | 1/1982 | Blazek | |
| 4,645,340 A | 2/1987 | Graham et al. | |
| 5,506,678 A | 4/1996 | Carlsen et al. | |
| 5,553,616 A | 9/1996 | Ham et al. | |
| 5,754,289 A | * 5/1998 | Ozaki et al. | ................ 356/301 |
| 6,167,290 A | 12/2000 | Yang et al. | |

FOREIGN PATENT DOCUMENTS

| | | |
|---|---|---|
| EP | 0 557 658 A1 | 9/1993 |
| JP | 2001165772 | 6/2001 |
| WO | WO 97/23159 | 7/1997 |
| WO | WO 97/36540 | 10/1997 |

\* cited by examiner

Primary Examiner—Eric F. Winakur
(74) Attorney, Agent, or Firm—Brinks Hofer Gilson & Lione

(57) ABSTRACT

The present invention provides an apparatus for measurement of Raman scattered radiation comprising. The apparatus comprises at least one source of electromagnetic radiation for producing an electromagnetic radiation beam characterized by a narrow spectral width, an integrating cavity having an interior and an exterior, wherein a sample is placed in said interior. The integrating cavity further having at least one port for insertion of the sample in the interior and for transmission of the electromagnetic radiation into and out from the interior, the at least one port extending from the exterior to said interior of said integrating cavity. The integrating cavity also comprises a first optical element for transmitting the electromagnetic radiation into the interior of the integrating cavity through the at least one port, and a second optical element for collecting Raman scattered electromagnetic radiation from the sample through the at least one port. The apparatus also comprises a spectrum analyzer for determining spectral composition of the Raman scattered electromagnetic radiation, a detector for measuring the Raman scattered electromagnetic radiation; and a system for determining concentration of at least one chemical compound from the measured Raman scattered electromagnetic radiation. The apparatus may also comprise a radiation expanding element. A method for measuring the concentration of one or more chemical compounds in a sample using Raman scattering is also provided.

28 Claims, 5 Drawing Sheets

RAMAN SPECTROSCOPIC SYSTEM WITH INTEGRATING CAVITY

FIELD OF INVENTION

The invention relates to the field of non-invasive spectroscopic measurements of samples. More specifically the invention relates to the use of Raman spectroscopy for the analysis of samples.

BACKGROUND OF INVENTION

Raman spectroscopy is concerned with the phenomenon of a frequency change when photons of electromagnetic radiation are inelastically scattered by molecules. If the frequency of incident electromagnetic radiation is $v_o$ and that of scattered electromagnetic radiation is $v_r$, then the magnitude of the frequency shift or Raman shift $v_o-v_r=\Delta v$ is referred to as Raman frequency. The Raman process can be understood by assuming incident electromagnetic radiation consists of photons with energy $hv_o$. On collision with molecules, a photon may be elastically scattered without change of energy. This gives rise to the so-called "Rayleigh" scattering signal. In some cases, called inelastic, the collision causes the electromagnetic radiation scattering molecule to undergo a quantum transition from one vibrational level to another. Energy needed to make this transition is either taken from the scattered photon (if vibrational transition is from lower to higher energetic level) or transferred to the photon (if vibrational transition is from higher to lover energetic level). As a result, the energy of the scattered photon is different from that it initially possessed. Since, under normal conditions of temperature and pressure, the majority of molecules are in a non-excited state, the probability that a photon will transfer its energy to excite the molecule is greater than the probability of the photon gaining energy as a result of molecular relaxation. The change in the energy of the photon leads to proportional shift of its frequency. Hence, the frequency of scattered photon can be shifted up or down by some value $\Delta v$ from initial frequency $v_o$. Frequency shift caused by interaction of photon with molecule, resulting in change of the vibrational energy of the molecule is referred to as Raman shift.

The amount of energy that can be taken or transferred from a photon to a molecule during the Raman scattering process is equal to the energy needed to change the state of the molecule from one vibration mode to another. The number of modes in a given molecule is limited and the energy needed for transition from one mode to another is well defined. The number of modes and the transition energy between the modes depends on the structure of the molecule, that is to say, the kind and number of atoms in the molecule, their relative position within the molecule, the kind of bonds between them and so on. As a result, each molecule has a specific pattern of possible transition energies. When monochromatic radiation interacts with a large number of such molecules, the pattern of possible energetic transitions is imaged as a pattern of frequency shifts of scattered radiation relative to the frequency of the incident monochromatic radiation. This pattern is called a Raman spectrum and can be obtained by spectrum analysis of the scattered radiation. The analysis of the frequency shift pattern can give information on the kind of molecules involved. Furthermore, since the number of Raman scattered photons is proportional to the intensity of the incident electromagnetic radiation and the number of molecules interacting, the intensity of the scattered electromagnetic radiation can provide information on the concentration of particular species in the specimen. In particular, Raman spectroscopy has demonstrated a wide range of capabilities in the spectral analysis of organic molecules.

Various kinds of spectrum analyzers can be used for this purpose, but recently spectrometers with integrating photodiode or CCD arrays gain importance in the instruments working in the spectral sensitivity ranges of the applied arrays. The Raman scattered radiation is delivered to an entry port (entry slit) of the analyzer/spectrometer. Usually, the capability of the system to register a signal depends on the strength of the signal, which is proportional to the number of photons received at the detector. Thus the strength of the signal depends on the total number of photons available as well as the efficiency of the system to collect these photons and to channel them to the analyzer and detector. The collecting efficiency of any optical system is determined by the optical invariant (or étendue), which is defined as the product of the radiation beam area at its waist and the angular spread-out of the radiation beam which can be accepted and transferred to photodetector. In efficient optical systems, the étendue cannot be larger than the product of the detector area and the solid angle from which it can collect the radiation. For any given detector both these values are predefined and they set a physical limit to the collecting efficiency of the optical system. Once this limit is reached the only way to increase the signal is to increase intensity of the source, which in case of Raman process depends on intensity of delivered excitation, number of molecules involved and efficiency of the process.

There are two distinguishably different Raman processes: stimulated and random (or ordinary) which differ significantly in terms of efficiency. Stimulated Raman scattering can be very efficient but it occurs only when coherent electromagnetic radiation beam of very high power density, produced for example by a laser, coherently interacts with a large number of molecules. The stimulated scattered radiation is well contained in space and can therefore be easily collected, delivered to the spectrum analyzer and detected. Unfortunately, because of the high power density required, this approach can result in damage to live tissues and cannot be routinely used for in-vivo medical diagnosis (see for example U.S. Pat. No. 5,553,616).

Random Raman scattering takes place when molecules interact with non-coherent or coherent electromagnetic radiation of power density insufficient to produce the stimulated Raman effect. Its efficiency is determined by the probability of inelastic scatter of a single photon on a single molecule. This probability is very small and drops dramatically with increasing wavelength of the applied exciting radiation (energy decrease of incident photons). For this and other technical reasons, radiation with wavelengths, which corresponds to the far infrared is seldom applied for Raman excitation. Unfortunately, because of a competing fluorescence effect, application of radiation from the visible and UV ranges is also undesirable.

The probability of random Raman process is very low and Raman scattered electromagnetic radiation is distributed uniformly in space (there is no preferred direction). Furthermore, only a small part of the radiation can be collected due to limited capabilities of radiation collecting systems. As a result, the collected Raman signal is very weak and a lot of effort has been undertaken to increase the collecting efficiency of the applied optical system by increasing the collecting angle as much as possible. Unfortunately, this strategy has not met with much success for two main reasons. The first is that there is an absolute limit, to which the collecting angle can be increased. This collecting angle can not be larger than the full solid angle. In practice the collecting angle is usually many times smaller because of technical limitations. The second is that an increase in the collecting angle reduces the area and volume of the sample from which the scattered radiation can be efficiently collected. This results in reducing the number of molecules being in a field of view of a collecting system, and reduces the number of molecules from which the Raman scattered radiation can be efficiently collected. In this situation, illumination with exciting radiation of the sample area that is larger than that, from which the scattered radiation can be effectively collected, is wasteful and should not be applied. Therefore the option of increasing the signal through improvement of the collecting capability of the optical system is very limited. Application of non-imaging optical systems, which usually collect radiation from larger volumes, is less efficient, and does not solve the problem of weak signal obtained from Raman scattering. Therefore, other methods to increase signal are required.

One way to increase the signal is to increase the intensity of the exciting radiation in the sample volume, from which scattered radiation can be efficiently collected. Unfortunately, many samples, especially of organic origin, have a limited resistance to irradiance with electromagnetic radiation, and there exists a limit for power density beyond which the molecular bonds of the sample can be irreversibly damaged. Therefore, the product of the volume, from which radiation can be efficiently collected, and the maximum power density tolerated by the sample determines a maximum power, which can be reasonably applied for a given sample. Application of a radiation beam with larger power will not produce any gain, either due to the sample damage, or inefficient sample excitation. Because of low efficiency of the random Raman process, direct excitation is not very efficient from energetic point of view.

Another way to increase efficiency is to enforce multiple interaction of radiation with the sample. This idea is exploited in U.S. Pat. No. 4,645,340 which discloses the use of an internally reflective sphere to redirect an unused part of the radiation back to a centrally located sample. The sphere is purely reflective, and no scattering of the radiation by the sphere takes place.

U.S. Pat. No. 4,127,329 teaches a method to increase efficiency of the Raman process, using two or more spherical mirrors to multiply reflect excitation to a gaseous sample. There is no scattering of the radiation by the apparatus.

U.S. Pat. No. 5,506,678 discloses the use of a reflecting tube and a radiation collecting optical system. The radiation signal is collected and delivered to a spectrometer, following interaction between the radiation and a gas sample placed within the tube. There is no scattering of the introduced radiation by the reflecting tube itself.

Collectively, these references address the problem of increasing efficiency of the Raman process through multiple reflection and refocusing of exciting radiation by means of mirrors, and collection of the radiation with radiation collecting optics that are able to collect radiation from a limited volume. Because of the limited volume from which radiation can be efficiently collected, great care is required to increase the power density of exciting radiation in the volume and to increase the poser density in such a way to enhance the probability of Raman scattering process. Because of a limited number of molecules involved in Raman scattering, increasing the power density creates a danger of sample damage. If the samples demonstrate strong elastic scattering, then this approach, is applicable to very small samples only. None of the above identified publications suggests application of an integrating cavity to redirect scattered radiation to a sample, and to store radiation inside the cavity, until it finds a way out of the cavity through one of several possible ports, where one or more of the ports could be coupled with spectrum analyzer and detector.

In WO 97/23159 an integrating cavity is disclosed that is used for spectroscopic measurement. Broad band spectroscopic radiation of known spectral content is introduced into the integrating cavity containing a test sample, and the spectrum of radiation is modified due to absorption in the sample. The spectrally modified radiation is collected and subjected to analysis to obtain information on absorbance of the sample. This publication does not teach application of the integrating cavity for analysis of Raman scattered radiation.

In many applications, for example, the analysis of living human subjects, it is impractical to take a small sample and to place it in the center of a sphere. Furthermore, very often it is important to have a signal from as large an area, or volume, of the sample as possible to reduce the dependence on local variations in the properties of the sample. Due to limited resistance of some samples to high optical power, the signal, which can be obtained from a small sample, is often too weak to provide required information, and application of increased total power is therefore desired. Additionally, in some samples it is important to get the signal from deeper layers of the sample. None of these problems can be addressed with instrumentation presently used for Raman signal collection.

The present invention offers an alternative way for permitting the use of higher power electromagnetic radiation and for the efficient collection of Raman scattered electromagnetic radiation, and overcomes limitations of the prior art.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to the field of non-invasive spectroscopic measurements of samples. More specifically the invention relates to the use of Raman spectroscopy for the analysis of samples.

The present invention provides an apparatus capable of efficiently collecting Raman scattered electromagnetic radiation from large samples, using high power exciting radiation without damaging the sample and by providing exciting radiation that is expanded or scattered prior to reaching the sample, thus avoiding high local power density on any part of the sample Thus in one aspect of the invention there is provided an integrating cavity, which enhances the detection of Raman scattered radiation. The integrating cavity is part of an apparatus for characterizing, measuring, or both characterizing and measuring the concentration of at least one chemical component in a sample, the apparatus comprising;

a) an integrating cavity having an interior and an exterior, wherein the interior of the cavity has a property of back scattering of incident radiation and wherein a sample is placed in the interior, the integrating cavity having at least one sample port for insertion of the sample in the interior, at least one entry port for coupling transmission of electromagnetic radiation into the integrating cavity, and the at least one exit port for extraction of scattered radiation from the integrating cavity, all ports extending from the exterior to the interior of the integrating cavity;

b) a source of electromagnetic radiation characterized by a narrow spectral band;

c) a first optical element for delivering the electromagnetic radiation into the interior of the integrating cavity through the at least one entry port;

d) a second optical element for collecting Raman scattered electromagnetic radiation from the integrating cavity through the at least one exit port, and for delivering the Raman scattered electromagnetic for analysis;

e) a spectrum analyzer, for analysis of spectral composition of delivered radiation;

f) a detector for measuring the spectral composition of Raman scattered electromagnetic radiation; and g) a system for determining the composition, concentration, or both the composition and concentration of at least one chemical component from measured Raman scattered electromagnetic radiation.

The present invention also provides the apparatus as described above, further comprising a radiation expanding element for diffusing the electromagnetic radiation before it comes into contact with the sample.

In another aspect of the invention the electromagnetic radiation is diffused in a diffusion chamber prior to impinging on the sample. Accordingly, there is also provided an apparatus for chemical characterization of a sample and measuring the concentration of at least one chemical component in a sample, the apparatus comprising an integrating cavity wherein the interior comprises at least one diffusing wall separating the integrating cavity into a diffusing chamber, and a sample chamber adapted to receive the sample, the diffusion chamber and the sample chamber comprising each at least one port extending from the exterior to the interior and wherein a first optical element is delivered to the diffusing chamber and a second optical element is coupled with the sample chamber, the first and second optical elements being used to deliver and collect electromagnetic radiation, respectively.

In yet another aspect of the present invention, the apparatus comprising an integrating cavity is used for chemical characterization of a sample, for measuring a concentration of at least one substance in the sample, or a combination thereof, using Raman scattering, the method consisting of:

a) generating an electromagnetic radiation characterized by a narrow spectral band;

b) placing the sample in an integrating cavity having an interior and an exterior, the interior having an optical property of back scatter of incident electromagnetic radiation, wherein the sample is placed in the interior, the integrating cavity having at least one port extending from the exterior to the interior;

c) coupling the generated electromagnetic radiation into the integrating cavity through the at least one port;

d) expanding the electromagnetic radiation before the radiation comes into contact with the sample;

e) collecting the Raman scattered electromagnetic radiation from the sample through the at least one port;

f) spectrally decomposing the collected radiation by means of a spectrum analyzer;

g) determining the chemical composition, concentration, or both the chemical composition and concentration of the one or more substances in the sample.

The present invention also provides an integrating cavity comprising:

i) an interior and an exterior, wherein a sample is placed in the interior of the integrating cavity, the integrating cavity having at least one port for insertion of the sample in the interior and for transmission of electromagnetic radiation into and out from said integrating cavity, the at least one port extending from the exterior to the interior of the integrating cavity, and ii) a radiation expanding element for expanding the electromagnetic radiation beam before the electromagnetic radiation beam comes into contact with the sample.

Also embraced in the present invention, is an apparatus comprising an integrating cavity optically coupled with a spectrum analyzer and detector for measuring Raman scattered electromagnetic radiation.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein.

DETAILED DESCRIPTION OF THE INVENTION

Figure 1:
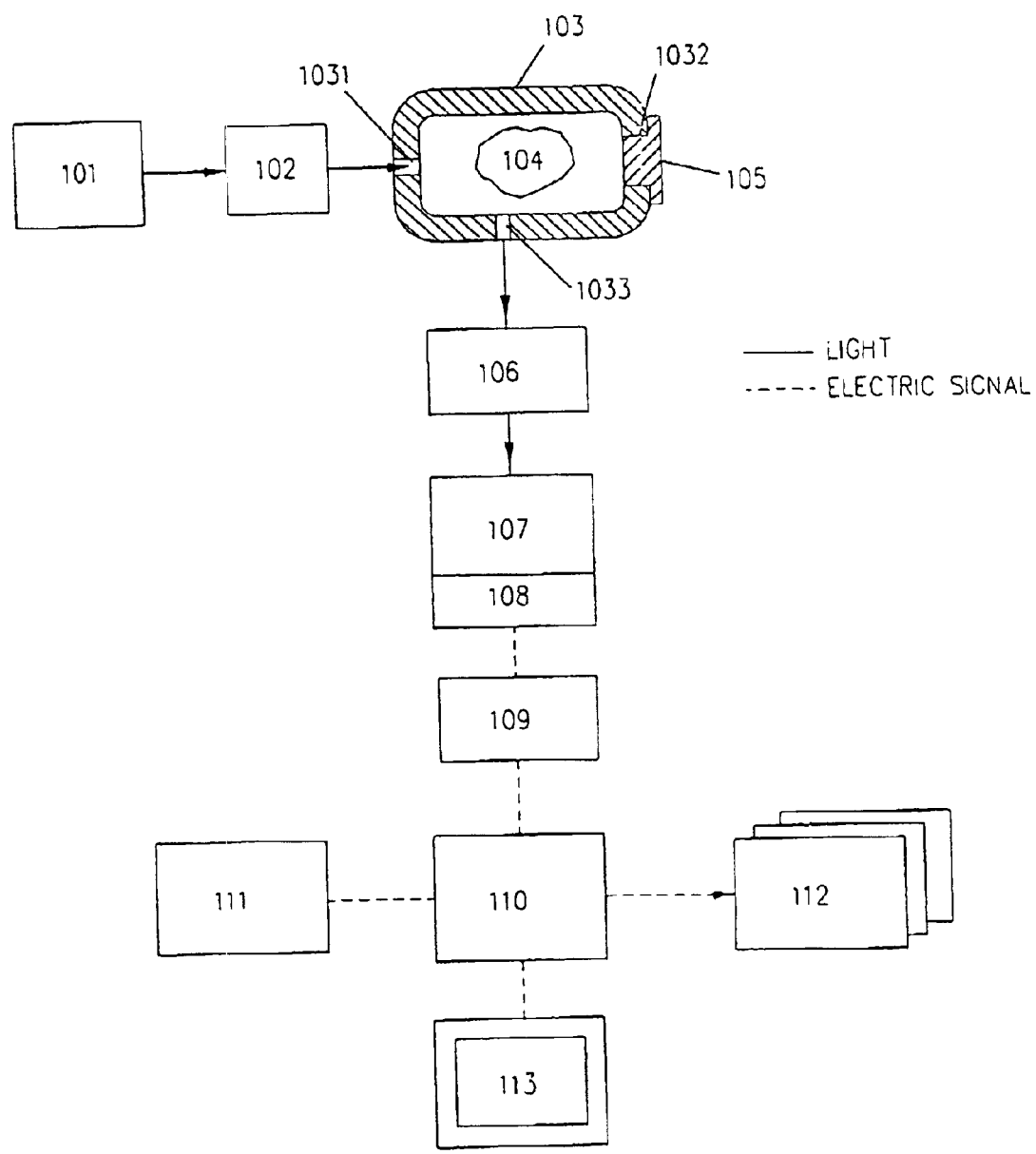
FIG. 1 is an illustration the general concept of the Raman spectroscopic system with integrating cavity. The figure shows application of the integrating cavity for injection into and extraction from a sample the electromagnetic radiation participating in Raman process, together with essential parts of a Raman spectrometer.

The present invention relates to the field of non-invasive spectroscopic characterization and measurements of the chemical composition of samples. More specifically the invention relates to the use of Raman spectroscopy and an integrating cavity for the analysis of samples.

The invention provides an apparatus capable of efficiently collecting Raman scattered electromagnetic radiation from a range of samples, including large samples that have been excited with high level of total power of radiation. In this case, the high power beam of electromagnetic radiation is expanded prior to reaching the sample, thus avoiding high local intensity on any part of the sample.

The following description is of a preferred embodiment by way of example only and without limitation to the combination of features necessary for carrying the invention into effect.

According to one aspect of the present invention, Raman spectroscopy may be used to characterize the chemical composition of a sample, measure the concentration of one or more substances in a sample, or both for example but not limited to samples sensitive to high power density electromagnetic radiation such as biological samples including body fluids, gases, tissues, or other organic samples, or any other sample such as but not limited to food, plastics, petroleum products, vapors of various substances, polluted air and the like. The sample may be a part of the body, such as but not limited to, a digit, such as a finger, which is placed in an integrating cavity, the properties of which will be described below.

According to the present invention, an integrating cavity is provided for the collection of Raman scattered electromagnetic radiation from various samples, including biological fluids and tissues exhibiting varying chemical components and concentrations of substances of interest. The resulting spectra are used to extract information on the identity and concentration of the chemical components in the sample by applying known chemometric methods. By chemometric methods it is meant any method used to independently measure the concentration of a chemical component and correlate this measurement with the intensity of the Raman spectra at specific wavelengths. Useful absorption bands of Raman spectra for biological samples are typically between about 50 and 10000 $cm^{-1}$ and are preferably between 150 and 8000 $cm^{-1}$.

The sensitivity of samples, for example but not limited to organic or biological samples, to high power electromagnetic radiation limits the specific radiation power density (watts per unit volume of sample: $W/cm^3$), or, if pulse illumination is applied, the specific energy density (joules per unit volume of sample: $J/cm^3$) that can be applied when Raman spectroscopy is used to analyze such samples. If the tolerance limits of either specific power, or specific energy are known for a sample, the total power or energy that can be applied to the sample can be calculated by multiplying the specific power or energy limits of the sample by the total volume of the sample.

By "tolerance limit" it is meant the amount of radiation power or energy level that can be applied to a unit volume or a unit surface of the sample without damaging the chemical bonds, or the structure of the molecules of the sample, or, if the sample is a living sample, for example but not limited to a digit, without providing discomfort to the patient. As would be apparent to one skilled in the art, the tolerance limit depends on the nature of the molecules and the amount of damage that is acceptable for a given sample. Sample damage levels due to electromagnetic radiation can vary by many orders of magnitude depending on the sample, the exposure time, and the wavelength of applied radiation, from a fraction of watt of continuous wave (CW) radiation per square centimeter for biological samples, to many kilowatts per square centimeter in the case of some transparent materials. Some samples may withstand up to several dozens of GW of radiation per square centimeter for very short pulses. International norms are established for limits of exposure of body parts to radiation. These standards are well known in the art and can be used as a guide for determining the power or energy level of exciting radiation that can be used. A predetermined tolerance limit can therefore be readily selected.

Prior art methods for collecting scattered radiation, collect radiation from a small volume to which only low levels of total exciting power, or energy, can be effectively applied without sample damage.

Any exciting radiation that inadvertently leaves the volume, from which scattered radiation can be efficiently collected, does not contribute to the collected signal. Since the efficiency of Raman scattering process is very low, it is desirable to illuminate, and enforce multiple interactions of the radiation with the sample, and collect Raman scattered radiation from a larger sample volume. However, illumination of a larger sample volume in the apparatus that is not optimized to capture the scattered radiation from such a volume is counterproductive, since scattered radiation from the sample cannot be collected by the radiation collecting system and it does not contribute (or contributes very weakly) to the registered signal. In case of samples with a strongly back scattering surface, the situation becomes even worse, since a large percentage of radiation may not even enter the volume of the sample, from which scattered radiation can be collected.

According to an aspect of the present invention, the limitations identified above can be to overcome by applying an integrating cavity, for example, which is not to be considered limiting in any manner, as disclosed in WO 97/231159 (which is incorporated herein by reference). An integrating cavity is usually made in a form of a shell with a wall characterized as non-absorbing, but that highly scatters the electromagnetic radiation. The integrating cavity acts as a radiation accumulator, ensuring that radiation repeatedly reflects between the walls, until it either diffuses through, or is absorbed by, the walls, is absorbed by the sample, or leaves the cavity by any unplugged port. The fate of the electromagnetic radiation within the cavity is the same for elastic and non-elastic (Raman) scattered radiation. It is to be understood that the integrating cavity disclosed in WO 97/231159 (which is incorporated herein by reference) may be used as described herein. However, as one of skill in the art will realize upon reading the criteria of an integrating cavity discussed below, any integrating cavity that optimizes interaction of exiting radiation with the sample, and that preferably ensures efficient collection of Raman scattered radiation produced from the sample, may be used in accordance with the present invention.

If the exciting radiation is not absorbed, it has a chance to interact with the sample many times, hence increasing the probability to be Raman scattered. Even if the sample scatters exciting radiation, the radiation cannot easily leave the cavity and is forced to be multiply reflected inside, thereby increasing the likelihood of Raman scattering by the sample. It is clear, that the probability of interaction of radiation with the sample increases when the ratio of the sample to the cavity volume tends to one. Therefore it is preferred that an integrating cavity of a size comparable to the sample size is used. If the shape of the sample cannot be modified to fit the cavity, as, for example, in case of the living subjects, a cavity of a shape conformal to that of the sample can be used.

Raman scattered radiation remains in the cavity unless it is absorbed by the sample or it finds a way to leave the cavity. If the absorption by walls and the sample is low, radiation remains in the cavity until it reaches some unplugged port, for example a port, from which radiation is collected for analysis. Therefore, it is desired that ports should be made as small as possible, and if some ports are not used during measurements they should be plugged with non-absorbing, back scattering material to prevent undesirable loses of radiation. In some cases, the sample itself can be used to plug a port, for example a sample port. The number of ports can be minimized by combining two or more ports together, by minimizing their cross sectional area, or by application of suitable optics for radiation injection into and extraction from the cavity. In particular, optical fibers can be used to deliver the electromagnetic radiation into, and to collect any Raman scattered radiation from, the integrating cavity. In cases, where the position of the sample in the cavity, or its size and shape vary, a plurality of entry and exit ports may be used to optimize system response to these variations. This can be easily realized by using multiple branches of optical fiber bundles which allow for the simultaneous delivery, or collection, of radiation to or from many points within the integration cavity.

The use of an integrating cavity for Raman spectroscopy such as those applied in absorption spectroscopy, for example but not limited to that disclosed in WO 97/23159, ensures multiple interaction of radiation with the sample. Furthermore, by using an integrating cavity any radiation scattered by the sample, including large samples, will eventually reach the exit port for collection by the collecting optics and then delivered to a spectrum analyzer for further analysis.

Since the total power (or energy) that can be delivered to the sample without damaging it is proportional to the volume of the sample, a significant gain can be achieved by increasing sample size. There are several advantages in using larger samples. One of them is an increased number of molecules involved in Raman scatter, resulting from a longer optical path on which exciting radiation can interact with the sample, thereby contributing to a stronger Raman signal. A second advantage is the possibility of using increased total power or energy provided to the sample. This advantage may be realized by ensuring that the energy is distributed evenly across the volume of the sample so that any given unit volume of the sample is not exposed to a power above its tolerance limit. A third advantage is the higher probability that scattered radiation will interact many times with the sample in the integrating cavity, thereby increasing the probability of obtaining a stronger signal from the sample. These advantages are particularly important when samples with low concentration of chemical components, like gases or vapors are tested. Another advantage is that by averaging of results over larger volume, the measurements are less susceptible to sample non-uniformity, and the ability to obtain a signal from deeper layers of the sample is increased. This is advantageous for the analysis of samples with non-uniform distribution of chemical components (or analytes), for example but not limited to glucose, cholesterol and other analytes measured in living humans.

Furthermore, an increase in the Raman signal can be obtained by using exciting radiation of high total power without adverse effects to the sample, by distributing the energy or power deposition over a substantial area or volume of the sample. Thus, the total power or energy received by the sample at any particular location remains below the tolerance limit, while the integrated total power or energy received over the entire volume of the sample may many times exceed the total power or energy reasonably applied to the volume from which radiation can be efficiently collected in the present art systems. Preliminary expansion of exciting radiation with a lens or an optical fiber or its scattering by a radiation expanding element in conjunction with walls of the cavity eliminates local concentration of radiation power or energy and reduces the probability of sample damage due to exceeding the radiation damage threshold of the sample. The sample damage level varies by many orders of magnitude depending on the sample, exposure time and wavelength of applied radiation: from a fraction of watt of CW radiation per square centimeter for biological samples, to many kilowatts per square centimeter in case of some transparent materials. Some of these materials may withstand up to several dozens of gigawatts of radiation per square centimeter for very short pulses.

Uniform distribution of the radiant energy may be accomplished by inserting the sample or a substantial portion of it into an integrating cavity made of scattering and/or reflecting material. The sample is then irradiated with a high power electromagnetic radiation beam, the power of which is distributed over a substantial area of the sample by means that will be described below. Electromagnetic radiation that has not interacted with the sample during a first pass through the sample is back scattered on the walls of the integrating cavity. This process is repeated many times, significantly increasing the probability that particular photons will interact with the sample and be scattered through the Raman process. At the same time, the Raman scattered electromagnetic radiation is also back scattered on the cavity walls to stay within the cavity, until it is absorbed by the sample, lost in other ways, or until it finds its way to the one or more radiation collecting (output) ports that then transmit the Raman scattered electromagnetic radiation to a spectrum analyzer and detector for measurement and further analysis.

The multiple back scattering of electromagnetic radiation on the cavity walls also creates a relatively uniform radiation field inside the cavity. As a result, the signal collected from the cavity is less sensitive to sample position within the cavity. This is advantageous when the sample is a living organism, or its body part, whose position cannot be easily maintained.

Therefore, the present invention provides an apparatus for the chemical characterization and concentration measurement of at least one chemical component (or analyte) in a sample, comprising;

a) at least one source of electromagnetic radiation for producing an electromagnetic radiation beam characterized by a narrow spectral width;

b) an integrating cavity having an interior and an exterior, wherein the sample is placed in the interior, the integrating cavity having at least one port for insertion of the sample in the interior and for transmission of the electromagnetic radiation, the at least one port extending from the exterior to the interior of the integrating cavity;

c) a first optical element for delivering the electromagnetic radiation from the radiation source into the interior of the integrating cavity through the at least one port;

d) a second optical element for collecting Raman scattered electromagnetic radiation from the sample through the at least one port;

e) a spectrum analyzer for determination of spectral composition of the Raman scattered radiation;

f) a detector for measuring the Raman scattered electromagnetic radiation; and g) a system for determining the analyte concentration from measured Raman scattered electromagnetic radiation.

Optionally, the apparatus may also comprise a radiation expanding element for expanding the electromagnetic radiation beam before the electromagnetic radiation beam comes into contact with the sample.

In this context "narrow spectral width" means a spectral width narrower than the required resolution of the measured Raman signal. Hence if the Raman shift has to be resolved with a certain resolution (5 cm$^{-1}$, for example), the spectral width of a radiation band used for excitation should not be wider than the required resolution. Preferably the spectral width should be about 2 times narrower than the required resolution. In the above example, which is not to be considered limiting in any manner, the spectral width should be narrower than 5 cm$^{-1}$, preferably, less than 2.5 cm$^{-1}$. Electromagnetic radiation of a narrow spectral width can be generated by any suitable means, for example but not limited to a laser, a light emitting diode, a superluminescent diode or any other source capable of providing a beam of sufficient power in the required spectral band.

By a "radiation expanding element" it is meant any device or system that reduces the level of power density of the exciting (input) electromagnetic radiation at any given point on the sample, in comparison to that from the total input power provided to the integrating cavity. For example, which is not to be considered limiting in any manner, a radiation expanding element may comprise a lens or an optic fiber designed to expand the cross-sectional area of an electromagnetic radiation beam and produce an expanded beam having a lower power or energy density per unit surface than the non-expanded beam. The power, or energy density, of the electromagnetic radiation beam at a given unit volume of the sample may also be reduced by separating the exciting beam using a plurality of optical fibers. Alternatively, a high power beam may be diffused by impinging upon a diffusion wall that scatters the input beam, before the beam comes into contact with the sample thereby reducing the power density of the input beam at any given point on the sample. The diffusing wall may be located within the integrating cavity, between an input port and the sample, or the diffusing wall may be located within the radiation delivering system, for example the optical element delivering the input beam, for example at an end of an optic fiber. The diffusing wall can comprise, but is not limited to: a ground plate made of any non-absorbing material for example but not limited to: a plate of glass, fused silica, quartz, sapphire, transparent plastic or any other similar material that may be coated, and with one or both randomly ground surfaces as a result of chemical etching or mechanical processing; a similar plate made of similar materials with a redistribution structure comprising either regular or random micro-grooves or micro-roughness, respectively on one or more surfaces to assist in the spatial radiation redistribution of electromagnetic radiation, and generally known diffractive optical elements, produced by hot or cold stamping, pressing, etching and so on; a plate made of non-absorbing material containing radiation scattering centers (for example, opalescent glass, TEFLON™, polytetrafluoroethylene (PTFE), SPECTALON™, or other radiation scattering materials); a radiation expanding element made of a non-absorbing plate covered with radiation scattering layer, for example, a plate of transparent plastic coated or painted with special radiation scattering material or covered with a layer of non-absorbing material containing radiation scattering centers, or radiation scattering centers produced by some optical means, for example but not limited to photolithography, holography, laser writing, laser assisted etching or any similar method.

In FIG. 1 there is shown an aspect of the present invention for measuring Raman scattering from a sample. Electromagnetic radiation, characterized by a narrow spectral width, is generated at a source 101 and directed into integrating cavity 103 of a desired shape through input (entry) port 1031. The integrating cavity contains a sample 104 introduced through port 1032 (sample port), which can be plugged with an electromagnetic radiation scattering, or a reflecting and scattering, plug 105. Scattered electromagnetic radiation, including Raman scattered radiation may exit through output (exit or radiation collecting) port 1033. Ports 1031, 1032 and 1033 can be combined to reduce the number of ports. For example, the cavity may contain a single port that serves as an input port for electromagnetic radiation and as a sample port to introduce the sample in the interior of the cavity, or the cavity may comprise more than one input port.

Radiation exiting port 1033 is collected by a collecting element 106 (second optical element). The collecting element may also be inserted within the integrating cavity to collect a part of the scattered electromagnetic radiation from the cavity interior and to direct it to an optical spectrum analyzer 107, which in turn is connected to a detector 108, which can be, but is not limited to, a photodetector array such as a linear diode array, a charge coupled device (CCD), a photodiode or a photomultiplier. The spectrum analyzer may be but is not limited to a spectrometer, a Fourier transform spectrometer, a tunable filter, acousto-optic tunable filter or a variable transmittance filter. Alternatively, the radiation reaching port 1033 can be directly detected by a detector 108. It is to be understood that there may be more than one radiation exiting ports, separately or individually connected to the spectrum analyzer and detector.

The detector is linked to a data collection unit 109, containing electronic components for extracting signals from the detector, and an analogue to digital converter for presentation of data in a digital form. The digitized data from the data collection unit is transferred to a data processing unit 110, which may perform data preprocessing or processing or may prepare data for presentation. The results can be further processed, locally stored in memory bank 111, transferred to external users 112 for further processing or presented to an operator by means of a user interface 113.

Figure 2:
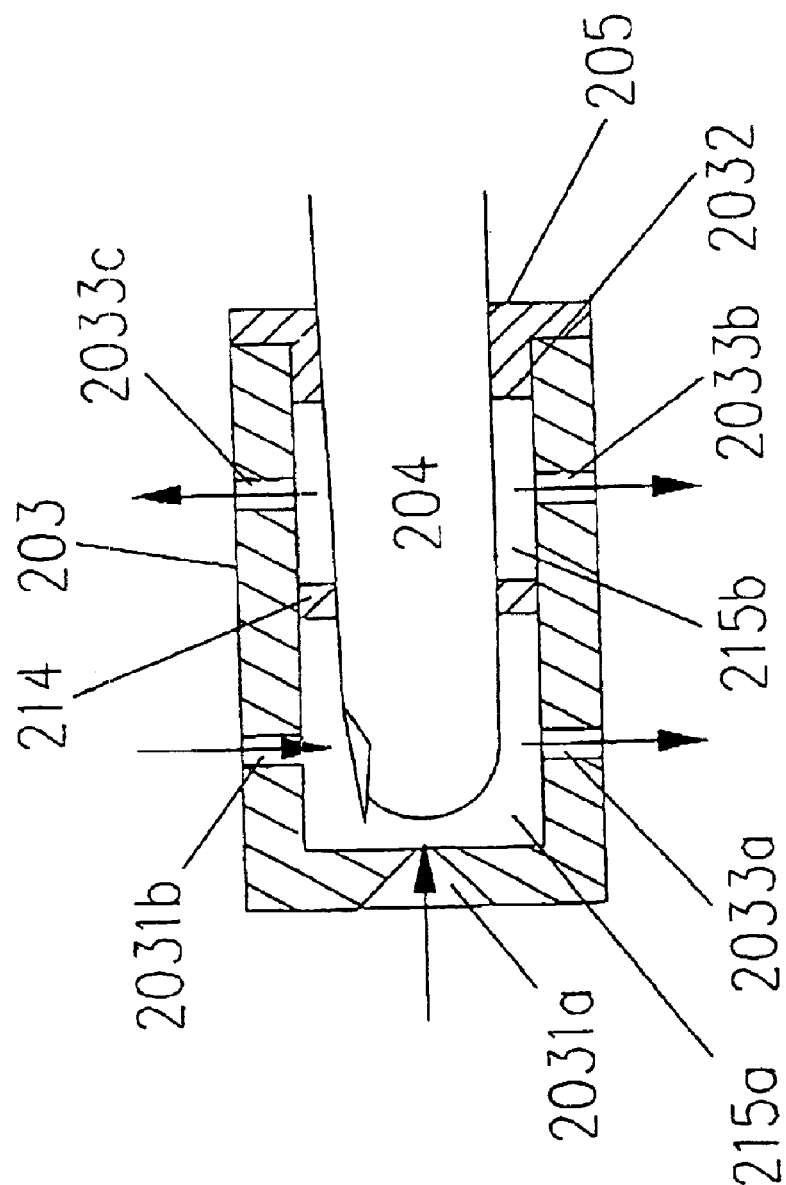
FIG. 2 illustrates a general concept of integrating cavity through a particular implementation of the cavity divided into two separate chambers by means of a electromagnetic radiation baffle, with plurality of electromagnetic radiation injection and electromagnetic radiation collection ports placed on both sides of the baffle, for Raman testing of chemical composition of human finger.

The integrating cavity will now be further described having regards to an embodiment in which the sample is a finger as shown in FIG. 2.

While integrating cavities of any desired geometrical shape can be considered, cavities of spherical shapes are preferred for liquid and gaseous samples. Without wishing to be bound by any theory, spherical symmetry enables an optimum number of molecules to interact with the reflected and/or scattered exciting electromagnetic radiation. However it has been noted that with solid samples, cavities with a shape similar to that of the sample being analyzed and having a volume slightly larger than the volume of the sample may provide a more intense signal. Thus, according to a preferred embodiment, the cavity size is minimized to substantially match the size of the sample while at the same time being large enough to allow electromagnetic radiation to be scattered on the cavity walls and uniformly illuminate the sample. The probability of a particular photon undergoing Raman scattering by a sample that substantially fills the cavity is greater than if the sample occupies a small volume of the chamber, since the probability of a photon interacting with the sample is greater in the first case. For example, a human finger 204 may be inserted in a cylindrical cavity 203.

The cavity comprises an interior delimited by an internal surface and an exterior delimited by an external surface. The entire cavity 203 can be made of non-absorbing scattering material such as but not limited to polytetrafluoroethylene (PTFE), SPECTRALON™, TEFLON™, electromagnetic radiation scattering glass or ceramic or a combination of these materials. Alternatively, the cavity may be made of any suitable material as would be obvious to one skilled in the art but with the internal surface covered with electromagnetic radiation scattering materials such as PTFE, SPECTRALON™, TEFLON™, electromagnetic radiation scattering glass or ceramic (for example but not limited to ground glass or ground ceramic), MgO, $BaSO_4$ or electromagnetic radiation scattering coating, deposits, paints, or a combination of these materials. In another embodiment, the cavity may be made of any suitable material but with the internal surface being finely-grounded or micro-grounded with a regular (for example, micro-grooves) or random (for example micro-roughness) redistribution structure, and covered with a highly reflective coating. The highly reflective coating may be, but is not limited to one or more dielectric layers, gold, aluminum, silver and other coatings used for surface reflection enhancement and protection. It is also within the scope of the present invention that the cavity be comprised of a non-absorbing scattering material which further comprises a redistribution structure of a finely-ground or micro-ground interior, exterior, or both interior and exterior surface with a regular or random micro-grooves or micro-roughness, respectively, and covered with a highly reflective coating. The choice of the cavity material and coating material will depend on the spectral range of the application as would be obvious to one skilled in the art.

By highly reflective, it is meant that the reflectance of the material or of the combination of materials should preferably be over 95% in selected working spectral range, which depending on application may lay anywhere in spectral range from far UV to far infrared, approximately between 150 and 25000 nm.

In yet another aspect of the present invention, the cavity can be made of material transparent to electromagnetic radiation such as but not limited to glass, fused silica and sapphire with the internal surface either being smooth or having rough, radiation scattering structure while the external surface comprises a rough, radiation scattering structure, for example a regular or a random redistribution structure, and being covered with highly reflecting coating. Preferably, the cavity, as just described, should be installed in a protective container.

It will be appreciated that the amount of electromagnetic radiation back scattered in any of the above-described embodiments of the cavity has to be sufficient to contribute to generation of a measurable Raman scattered radiation at the detector. Thus, the thickness and the nature of the material of the cavity wall, or coating should be chosen to achieve an adequate Raman signal in the spectral range of interest. The optical properties of the materials enumerated above are well known in the art.

The cavity may contain a single or a multiplicity of input ports 2031*a*, 2031*b* for transmission of exciting electromagnetic radiation into the cavity, one or more port 2032 for sample 204 introduction into the cavity 203, and one or a multiplicity of output ports 2033*a*, 2033*b*, 2033*c* to collect electromagnetic radiation from the cavity. If the sample is completely contained in the cavity the sample port can be completely closed with an electromagnetic radiation reflecting or scattering plug or, if the sample protrudes outside the cavity, the sample itself can play the role of a plug, which can be supported by an additional seal 205. It will be appreciated that a single port may be used for transmission and collection of electromagnetic radiation and for insertion of the sample in the chamber. In some cases it may be advantageous that the sample port and the transmission (input) and/or collecting (output) port be physically separated. Also, the ports may consist of a material transparent to electromagnetic radiation in a given spectral range, and sealed in place to ensure a sealed cavity. This may allow for example, the inclusion of liquid or gaseous samples into the cavity that fill the cavity volume.

The relative position of transmission ports can vary. The ports may be used to transmit radiation into the cavity or to collect radiation from the cavity. In particular, a single port can be used for both purposes, and the path of transmitted and collected electromagnetic radiation beams can be separated outside of the cavity by means of a partially transparent mirror for example, whose transparency can be either uniform or non-uniform across the spectrum. In particular, a dichroic mirror, narrow band holographic mirror or notch filter can be used to separate exciting radiation from Raman scattered radiation components. In another aspect, it is possible to use independent ports in association with suitable optical elements to transmit, collect and relay electromagnetic radiation from the integrating cavity to a spectrum analyzer. Optical elements such as but not limited to lens, mirror and radiation guide can be used. For example, optic fibers directly inserted into cavity walls can be used for electromagnetic radiation transmission and collection. It will be obvious, for those skilled in the art, that there is no need to use identical elements for electromagnetic radiation transmission and collection. It is possible to envision a system in which electromagnetic radiation is directly transmitted into the cavity, while optical fibers are used to collect Raman scattered radiation from the cavity or vice versa.

A further advantage of the integrating cavity of the present invention is to reduce the amount of background noise at the detector. That is to say, the design of the cavity should be optimized to reduce the amount of radiation other than radiation scattered by the sample in a Raman fashion. In this respect, if the electromagnetic radiation is transmitted into the cavity in such a way that it can directly impinge on the output port without being scattered by the sample, a strong background of non Raman scattered electromagnetic radiation can be produced that reduces the signal to noise ratio. To reduce this background, one or more ports used for electromagnetic radiation transmission into the cavity (input ports) and one or more ports used to collect the scattered radiation (output ports) should be located outside their respective fields of view. For example, which is not to be considered limiting in any manner, one or more input ports and one or more output ports may be located within separate chambers within the integrating cavity of the present invention, thereby reducing background, at the same time providing more uniform, diffuse illumination of the sample.

Reduced background and more uniform sample illumination can also be achieved by using an electromagnetic radiation scattering baffle 214 dividing the cavity into two or a larger number of separate sub-cavities (chambers) 215*a*, 215*b*. The baffles can be used to reduce direct coupling of exciting electromagnetic radiation with the detector, thus reducing background signals caused by electromagnetic radiation that has not interacted with the sample.

Figure 3:
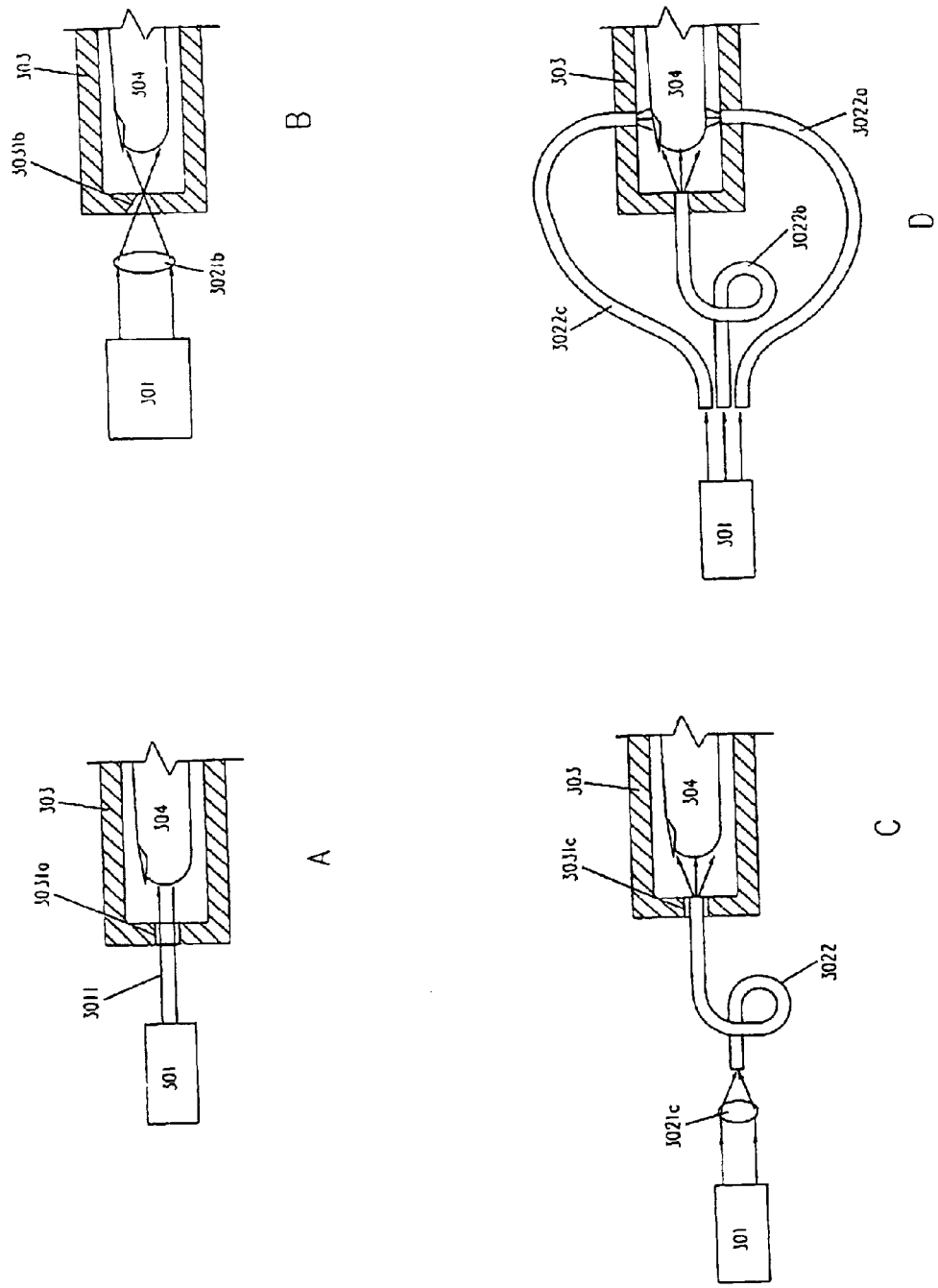
FIG. 3 illustrates various ways to deliver electromagnetic radiation to the sample in integrating cavity. Similar approaches can be used for electromagnetic radiation extraction from the cavity.

Now, referring to FIG. 3, alternate aspects of the present invention are described. Exciting electromagnetic radiation can be transmitted into the cavity either directly through port 3031*a* of diameter comparable to diameter of the applied laser beam 3011 (FIG. 3A), or by means of lens 3021, which focuses the radiation into a small port 3031*b* in the cavity wall 303 (FIG. 3B). The electromagnetic radiation from the laser 301 (FIG. 3C) can also be transmitted by means of lens 3021c into a radiation guiding element, for example but not limited to an optical fiber 3022, which delivers electromagnetic radiation to the integrating cavity 303 through the small transmission port 3031c in the cavity wall. Other means of transmitting electromagnetic radiation into the cavity as would be obvious to one skilled in the art are also contemplated to be within the scope of the invention.

As mentioned above the beam of electromagnetic radiation is preferably expanded to reduce the local power density at any point of the sample. The electromagnetic radiation, transmitted into the cavity by means of the lens or the radiation guiding element, (as shown in FIGS. 3B and 3C), produces an expanded electromagnetic radiation beam, whose intensity on the sample surface can be significantly smaller than that produced by non-expanded or a highly focused laser beam (shown in FIG. 3A). The local power or energy density of the beam can also be reduced by separating the beam using two or more optic fibers as shown in FIG. 3D. Because the power density at any given point on the sample is lower when using a spread laser beam, the total power that can be applied for Raman excitation without damaging the sample is higher and consequently produces a stronger signal.

Electromagnetic radiation collection from the cavity can be performed in a similar way as it is transmitted into the cavity. The electromagnetic radiation exiting a port can go either directly to the electromagnetic radiation analyzer or be transferred by means of an optical system. For example, which is not to be considered limiting, a focusing lens can be used to collect electromagnetic radiation emerging from the transmission port and to transfer it to the analyzer. Single or larger number of optical fibers, directly inserted into the transmission port can also collect electromagnetic radiation and deliver it for analysis.

Figure 4:
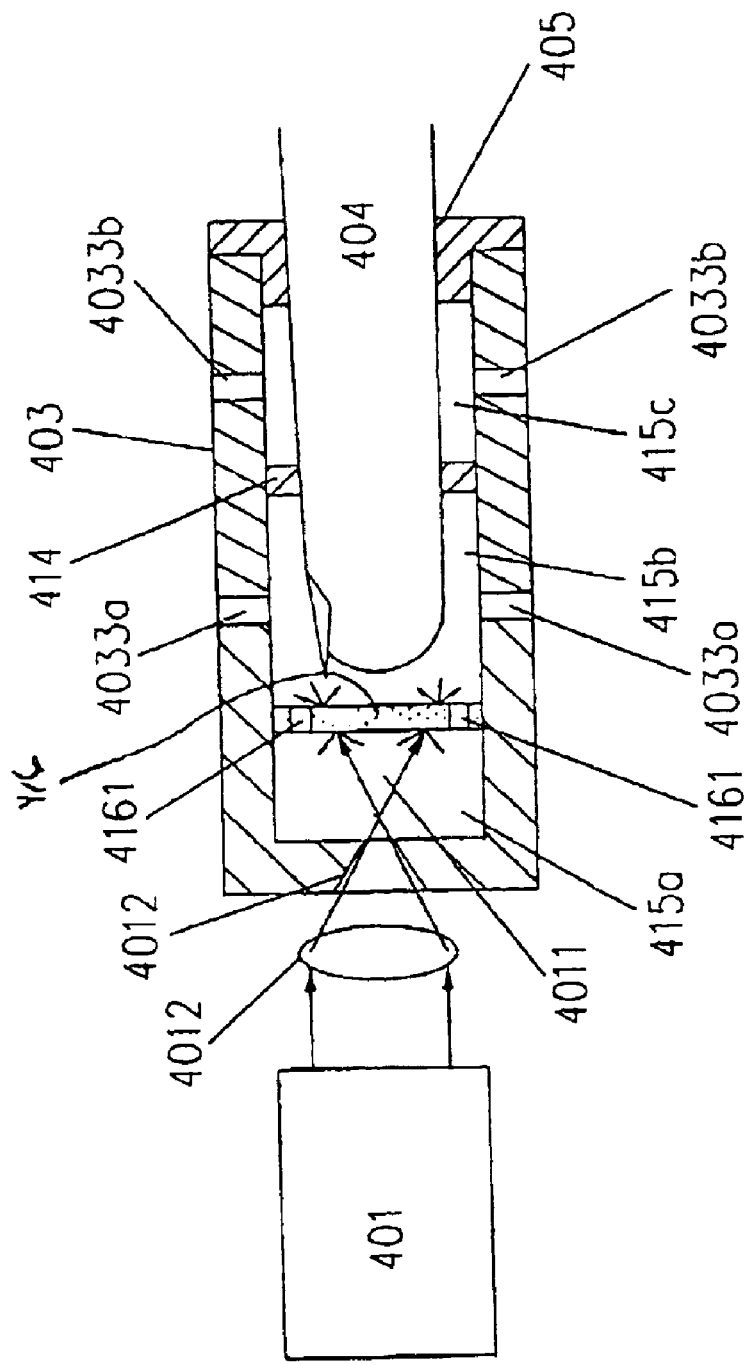
FIG. 4 illustrates as above but with additional baffle inside the cavity to eliminate exposure of the sample with direct exciting electromagnetic radiation in order to produce more uniform and lower power density illumination on the sample. At the same time the baffle is used as a position locator for the sample.

FIG. 4A shows an integrating cavity 403 consisting of at least two separate chambers: 415a and 415b. The first chamber 415a, is separated from the remaining part of the integrating cavity by a diffusing wall 416, which in some cases can also be used as a support for the sample. The diffusing wall may be comprised of an opaque or a scattering material. It is also within the scope of the present invention that the diffusing wall may be located within an optical element transmitting the input electromagnetic radiation beam into the integrating cavity, for example at an end of an optic fiber. In this embodiment, a secondary diffusing wall within the cavity may be used, if a further diffusion of the input beam is required. Baffles 414, which can be made of scattering material and can also provide support for the sample (finger) may be used to delimit a third chamber 415c.

The diffusing wall can be made of scattering materials as previously stated, such as but not limited to PTFE, Spectralon™, Teflon™, electromagnetic radiation scattering glass or ceramic or a combination of these materials. Furthermore, one or both surfaces of the diffusion wall may be finely-ground or micro-ground with a regular (for example, micro-grooves) or random (for example microroughness) redistribution structure, and covered with a highly reflective coating. The highly reflective coating may be, but is not limited to one or more dielectric layers, gold, aluminum, silver and other coatings used for surface reflection enhancement and protection. The diffusion wall may also be comprised of a non-absorbing scattering material which further comprises one or more surfaces that is finely-ground or micro-ground with a regular (for example, micro-grooves) or random (for example micro-roughness) redistribution structure, and covered with a highly reflective coating. The diffusion wall can also consist of a diffusion grating or any other radiation redistributing optical element. The electromagnetic radiation, entering the chamber 415a, reaches diffusing wall 416 and is scattered in all direction. The forward scattered electromagnetic radiation may diffuse through the wall and reach the second chamber 415b, where the sample 404 is placed. The majority of back scattered electromagnetic radiation reaches the walls of the chamber 415a and is back scattered in the direction of the diffusing wall 416, where the scattering process is repeated again. This process lasts until the electromagnetic radiation escapes from the first chamber and reaches chamber 415b. To facilitate the process of electromagnetic radiation transfer between the chambers, the diffusing wall 416 may contain holes outside of the area directly illuminated by the transmitted beam 4011, or the surface of the diffusion wall may be smaller than the cross-sectional area of the cavity, so that the diffusing wall is supported in front of the input beam path, yet allows scattered radiation past to the remaining cavity. Once electromagnetic radiation enters the chamber 415b, it interacts with the sample 404. Part of radiation reaching the sample is back scattered into the chamber, while another part penetrates inside the sample where it can be either partially absorbed, or scattered by different mechanisms, including Raman scattering. Because of the high back scattering property of the material used to create cavity walls, the electromagnetic radiation back scattered at sample surface, returns to the sample after one of more interactions with the cavity walls increasing chance to penetrate inside the sample and to be Raman scattered. This multiple scattering mechanism results in the sample being substantially uniformly illuminated with scattered electromagnetic radiation.

Since the exciting electromagnetic radiation is significantly scattered it loses its coherence and non-linear optical effects, which could cause damage to the sample, are dramatically reduced.

The wavelength of the applied electromagnetic radiation may advantageously be selected to be outside any major absorption bands of the sample, to reduce direct heating. This allows for the total power of the exciting radiation to be increased. The use of exciting radiation with a wavelength outside the absorption range of the sample has the additional advantage of more deeply penetrating into the sample, thus providing information on chemical components (analytes) located further away from the surface of the sample. In particular, if the method is applied for diagnostic of human body, this allows for deeper penetration of radiation into tissue and extraction of information on concentration of chemical components (analytes) inside the body, such as in blood, for example.

Figure 5:
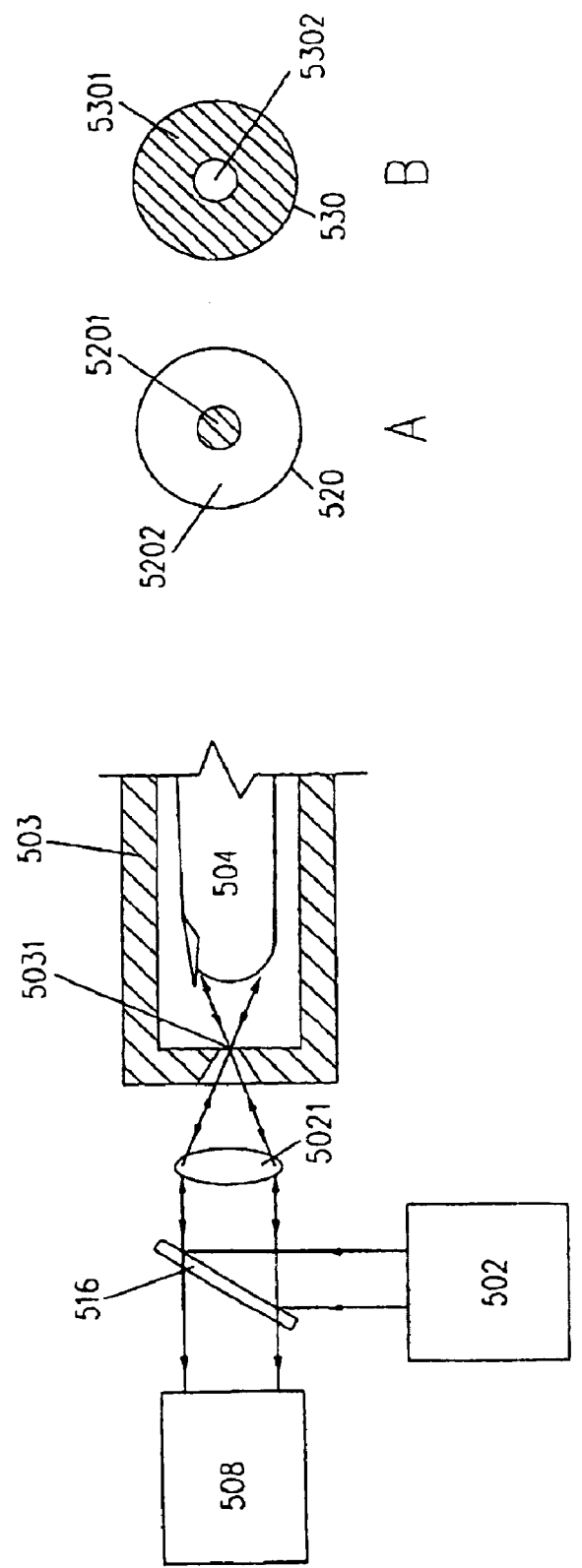
FIG. 5 illustrates a particular implementation of the cavity with a common electromagnetic radiation port used for both electromagnetic radiation delivery to and extraction from the sample.

FIG. 5 illustrates an example of a particular embodiment of the cavity 503 in which a common port 5031 for electromagnetic radiation transmission into the cavity and collection after scattering is used. Electromagnetic radiation from the delivery system 502 is reflected by a narrow band reflector 516 and focused by lens 5021 into port 5031 to reach sample 504. Raman scattered radiation of wavelengths different from that used for excitation is collected by the same lens, and then passes through the narrow band reflector 516, and reaches the radiation collecting system 508, which directs the radiation to the spectral analyzer. A narrow band holographic or thin layer dielectric mirror can be used as reflector 516, for example. One advantage of this embodiment is that the mirror reduces the amount of non-Raman scattered electromagnetic radiation, reaching the detector system. The position of the electromagnetic radiation delivery and collecting systems can be interchanged if instead of a narrow band reflector a narrow band, transmitting mirror is used. Various other elements can be used to separate the path of the exciting and scattered electromagnetic radiation beams. For example, a mirror 520 (FIG. 5A) with a small reflecting area 5201 can be used to reflect collimated exciting beam, while scattered electromagnetic radiation is transmitted through the non reflecting area around the reflecting part of mirror 5202. Alternatively, a mirror 530 with a small transparent hole 5302 and a large reflecting area 5301 can be used.

The integrating cavity may contain any number of non-absorbing but electromagnetic radiation scattering supports for positioning the sample within the cavity. These supports can be made of radiation scattering material or covered with material capable of efficient back scatter and/or reflection of the radiation.

While the above described embodiments emphasize the use of solid samples, the instant invention may also be applied to a liquid and gaseous samples. These samples can be encapsulated into transparent non-absorbing capsule or container and placed in the integrating cavity for measurement. Alternatively, liquid or gaseous samples may be directly incorporated into the cavity or flow through the cavity provided that the ports are properly sealed. Also, such samples can flow through a transparent, non-absorbing tube protruding through the walls of the cavity.

While the invention has been described with particular reference to measuring the concentration of analytes in biological samples in a non invasive way, it is to be understood that the technology can also be adapted to provide measurements of Raman spectra in any sample and in particular in photosensitive samples.

The above description is not intended to limit the claimed invention in any manner, furthermore, the discussed combination of features might not be absolutely necessary for the inventive solution.

While the present invention has been described with reference to what are presently considered to be preferred examples, it is to be understood that the invention is not limited to the disclosed examples. To the contrary, the invention is intended to cover various modifications and equivalents included within the spirit and scope of the appended claims.

All publications, patents and patent applications referred to herein are incorporated by reference in their entirety to the same extent as if each individual publication, patent or patent application was specifically and individually indicated to be incorporated by reference in its entirety.

What is claimed is:

1. An apparatus for measurement of Raman scattered radiation comprising:
   a) one or more than one source of electromagnetic radiation for producing an electromagnetic radiation beam characterized by a narrow spectral width;
   b) an integrating cavity comprising:
      (i) an interior and an exterior, wherein a sample is placed in said interior, said integrating cavity having one or more than one port for insertion of said sample in said interior and for transmission of said electromagnetic radiation into and out from said interior, said one or more than one port extending from said exterior to said interior of said integrating cavity, and
      (ii) a radiation expanding element for expanding said electromagnetic radiation before said electromagnetic radiation beam comes into contact with said sample;
   c) a first optical element for transmitting said electromagnetic radiation into said interior of said integrating cavity through said one or more than one port;
   d) a second optical element for collecting Raman scattered electromagnetic radiation from said sample through said one or more than one port;
   e) a spectrum analyzer for determining spectral composition of said Raman scattered electromagnetic radiation;
   f) a detector for measuring said Raman scattered electromagnetic radiation; and
   g) a system for determining a concentration of one or more than one chemical compound in said sample from Raman scattered electromagnetic radiation measured by said detector.

2. The apparatus according to claim 1 wherein said source of electromagnetic radiation is selected from the group consisting of a laser, a light emitting diode (LED) and a superluminescent diode.

3. The apparatus according to claim 1, wherein said integrating cavity comprises electromagnetic radiation scattering material of sufficient thickness to back scatter a sufficient amount of electromagnetic radiation into said interior of said integrating cavity to enhance production, and analysis, of Raman scattered radiation with said spectrum analyzer and detector.

4. The apparatus according to claim 3, wherein said electromagnetic radiation scattering material comprises electromagnetic radiation scattering material selected from the group consisting of: an electromagnetic radiation scattering opalescent glass, an electromagnetic radiation scattering material comprising polytetrafluoroethylene (PTFE), and an electromagnetic radiation scattering ceramic.

5. The apparatus according to claim 1, wherein said interior is delimited by an internal surface which comprises an electromagnetic radiation scattering coating of sufficient thickness to back scatter a sufficient amount of electromagnetic radiation into said interior of said integrating cavity to enhance production and analysis of Raman scattered radiation with said spectrum analyzer and detector.

6. The apparatus according to claim 5, wherein said electromagnetic radiation scattering coating comprises an electromagnetic radiation scattering material selected from the group consisting of: an electromagnetic radiation scattering material comprising polytetrafluoroethylene (PTFE) an electromagnetic radiation scattering ceramic, a layer of electromagnetic radiation scattering MgO, and $BaSO_4$.

7. The apparatus according to claim 1, wherein said interior is delimited by an internal surface comprising a redistribution structure and coated with one or more than one thin layer of an optical material that enhances reflection.

8. The apparatus according to claim 7, wherein said optical material is selected from a group consisting of: aluminum, silver, gold, and multiple dielectric layers.

9. The apparatus according to claim 1, wherein said integrating cavity is made of a material transparent to electromagnetic radiation with an internal, an external or both internal and external surface comprising a redistribution structure, wherein said internal, said external, or both of said internal and external surface is covered with one or more than one layer of a reflection enhancing material selected from group consisting of: aluminum, silver gold, and multiple dielectric layers.

10. The apparatus according to claim 1 wherein said first optical element and said second optical element are selected from the group consisting of a lens, a mirror, a radiation guiding element, and a combination thereof.

11. The apparatus according to claim 10 wherein said radiation guiding element is an optic fiber.

12. The apparatus according to claim 1, wherein said spectrum analyzer is selected from the group consisting of a spectrometer, a Fourier transform spectrometer, a turntable filter, an acousto-optic turntable, and a variable transmittance filter.

13. The apparatus according to claim 1 wherein said detector is selected from the group consisting of a linear diode array, a CCD, a photodiode, and a photomultiplier.

14. The apparatus according to claim 1, wherein said system for determining a concentration of one or more than one chemical compound in said sample from Raman scattered electromagnetic radiation measured by said detector comprises a computer comprising one or more than one calibration algorithm.

15. The apparatus according to claim 1, wherein said radiation expanding element is selected from a diffusion wall and a lens or a combination thereof.

16. The apparatus according to claim 15, wherein said diffusion wall comprises one or more than one aperture, said one or more than one aperture located outside a cross sectional area of said electromagnetic radiation impinging on said diffusion wall.

17. The apparatus according to claim 15, wherein said diffusion wall comprises a material selected from the group consisting of: an electromagnetic radiation scattering material comprising polytetrafluoroethylene (PTFE), an electromagnetic radiation scattering ceramic, an electromagnetic radiation scattering opalescent glass, a coated glass, a coated fused silica, a coated quartz, a coated sapphire, a coated transparent plastic, an electromagnetic radiation non-absorbing material, and one or more of a material with a redistribution structure on one or both surfaces.

18. The apparatus according to claim 17, wherein said integrating cavity comprises two or more than two ports coupled to said first optical element.

19. The apparatus according to claim 17, wherein said integrating cavity comprises two or more than two ports coupled to said second optical element.

20. The apparatus according to claim 1, wherein said integrating cavity comprises two or more than two ports and wherein said first and said second optical element are each coupled with a different port.

21. The apparatus according to claim 1, wherein said radiation expanding element comprises one or more than one diffusing wall separating said interior of said integrating cavity into a diffusing chamber and a sample chamber, said sample chamber for receiving said sample, said diffusion chamber and said sample chamber each comprising one or more than one port extending from said exterior to said interior and wherein said first optical element is optically coupled with said diffusing chamber and said second optical element is optically coupled with said sample chamber.

22. The apparatus according to claim 21, wherein said diffusion wall comprises a material selected from the group consisting of an electromagnetic radiation scattering opalescent glass, an electromagenetic scattering material comprising polytetrafluoroethylene (PTFE), an electromagnetic radiation scattering ceramic, a coated glass, a coated fused silica, a coated quartz, a coated sapphire, a coated transparent plastic, an electromagnetic radiation non-absorbing material, and one or more of a material with a redistribution structure on one or both surfaces.

23. A method for measuring a concentration of one or more than one chemical compound in a sample using Raman scattering comprising:

a) placing said sample within an integrating cavity comprising:
   i) an interior and an exterior, wherein a sample is placed in said interior of said integrating cavity, said integrating cavity having one or more than one port for insertion of said sample in said interior and for transmission of electromagnetic radiation into and out from said integrating cavity, said one or more than one port extending from said exterior to said interior of said integrating cavity, and
   ii) a radiation expanding element for expanding said electromagnetic radiation beam before said electromagnetic radiation comes into contact with said sample;
b) generating an electromagnetic radiation beam characterized by a narrow spectral width and transmitting said electromagnetic radiation into said integrating cavity;
c) directing said electromagnetic radiation beam through said integrating cavity so that before said electromagnetic radiation beam comes into contact with said sample an expanded beam having a specific radiation power density smaller than a predetermined tolerance limit for said sample is produced;
d) collecting Raman scattered electromagnetic radiation from said sample within said integrating cavity;
e) spectrally decomposing said Raman scattered electromagnetic radiation;
f) measuring said Raman scattered electromagnetic radiation; and
g) determining said concentration of said one or more than one chemical compound.

24. The method according to claim 23, wherein said sample is a digit.

25. The method according to claim 24, wherein said digit is a finger.

26. The method according to claim 25, wherein said one or more than one chemical compound is glucose.

27. The method according to claim 23, wherein said radiation expanding element of said integrating cavity comprises one or more than one diffusing wall separating said interior of said integrating cavity into a diffusion chamber and a sample chamber, said diffusion chamber and said sample chamber each comprising one or more than one port extending from said exterior to said interior and wherein in step b) said sample is placed in said sample chamber, in step c) said electromagnetic radiation is transmitted into said diffusing chamber through said one or more than one port of said diffusing chamber and in step d) said Raman scattered electromagnetic radiation is collected from said sample through said one or more than one port of said sample chamber.

28. An integrating cavity comprising:
a) an interior and an exterior, wherein a sample is placed in said interior of said integrating cavity, said integrating cavity having one or more than one port for insertion of said sample in said interior and for transmission of electromagnetic radiation into and out of said integrating cavity, said one or more than one port extending from said exterior to said interior of said integrating cavity, and
b) a radiation expanding element for expanding said electromagnetic radiation before said electromagnetic radiation beam comes into contact with said sample.

* * * * *